United States Patent
Shah et al.

(10) Patent No.: US 12,268,698 B2
(45) Date of Patent: Apr. 8, 2025

(54) HYBRID POLYVINYL ALCOHOL/ LINSEED DUAL CROSSLINKED NANOCOMPOSITE HYDROGEL LOADED WITH DOXYCYCLINE FOR THE PRODUCTION OF ACNE PATCHES

(71) Applicants: Muhammad Raza Shah, Karachi (PK); Maria Khalid, Karachi (PK); Tooba Jabri, Karachi (PK); Shafi Ullah, Karachi (PK)

(72) Inventors: Muhammad Raza Shah, Karachi (PK); Maria Khalid, Karachi (PK); Tooba Jabri, Karachi (PK); Shafi Ullah, Karachi (PK)

( * ) Notice: Subject to any disclaimer, the term of this patent is extended or adjusted under 35 U.S.C. 154(b) by 27 days.

(21) Appl. No.: 17/553,856

(22) Filed: Dec. 17, 2021

(65) Prior Publication Data
US 2023/0190771 A1    Jun. 22, 2023

(51) Int. Cl.
*A61K 9/06* (2006.01)
*A61K 31/65* (2006.01)
*A61K 47/02* (2006.01)
*A61K 47/32* (2006.01)
*A61K 47/46* (2006.01)
*A61P 31/04* (2006.01)

(52) U.S. Cl.
CPC ................ *A61K 31/65* (2013.01); *A61K 9/06* (2013.01); *A61K 47/02* (2013.01); *A61K 47/32* (2013.01); *A61K 47/46* (2013.01); *A61P 31/04* (2018.01)

(58) Field of Classification Search
CPC ....................................................... A61K 9/06
See application file for complete search history.

(56) References Cited

PUBLICATIONS

"Flaxseed Oil for the Skin." (Nov. 6, 2006). Accessed Jul. 12, 2023. Available from: < https://www.cherrypitpac.com/flaxseed-oil-for-the-skin.html >. (Year: 2006).*
"Nine Myths About Linseed Oil and Flaxseed Oil." (Jun. 12, 2020). Accessed Jul. 12, 2023. Available from: < https://treeboard.com/blog/nine-myths-about-linseed-oil-and-flaxseed-oil/ >. (Year: 2020).*
Park, Hyeon-Ho, et al. "Characterization and biological activity of PVA hydrogel containing chitooligosaccharides conjugated with gallic acid." Carbohydrate Polymers. (2018), vol. 198, pp. 197-205. (Year: 2018).*
"5 things you need to know about Zinc Oxide." (Jun. 11, 2020). Accessed Jul. 12, 2023. Available from: < https://www.lookfantastic.com/blog/discover/5-things-you-need-to-know-about-zinc-oxide/ >. (Year: 2020).*

* cited by examiner

*Primary Examiner* — John S Kenyon

(57) ABSTRACT

A nanocomposite hydrogel sheet and doxycycline loaded acne healing patches derived therefrom. The present invention relates to the biocompatible hydrogel sheet matrix comprising polyvinyl alcohol, linseed mucilage extract, nano zinc-oxide crosslinked dually via covalent linkages and free radical polymerization by e-beam exposure. The pore size of the nanocomposite hydrogel sheet ranges between 0.1-0.5 μm. The doxycycline loaded acne patches derived from nanocomposite hydrogel sheet were able to inhibit the growth of *S. aureus* in an in vitro bacterial growth inhibition assay.

5 Claims, 8 Drawing Sheets

HYBRID POLYVINYL ALCOHOL/ LINSEED DUAL CROSSLINKED NANOCOMPOSITE HYDROGEL LOADED WITH DOXYCYCLINE FOR THE PRODUCTION OF ACNE PATCHES

BACKGROUND OF THE INVENTION

1. Field of the Invention

The current invention relates to preparation of nanocomposite hydrogel sheet based on polyvinyl alcohol (PVA) and linseed (LS) mucilage extract and its application thereof. The synthesized hydrogel is being prepared as a doxycycline loaded acne extraction patch for cystic acne. As such the invention relates to the field of dermatological and acne care products.

2. Description of Related Art

Cystic acne is a type of acne that is characterized by painful, pus-filled pimples that appear deep beneath the skin. Acne is caused by oil and dead skin cells blocking skin pores. Bacteria infiltrate cystic acne sufferers' pores, causing swelling and inflammation. As a result, an acne cyst forms beneath the skin as a small "sac" filled with excess sebum (oil), bacteria, and dead skin cells. This "sac" is frequently surrounded by inflamed tissue with larger capillaries, causing them to protrude from the skin. Before they may be seen, cystic acne lesions are usually felt beneath the skin.

The most commonly prescribed treatments for cystic acne include oral antibiotics and topical antibiotic creams. Oral antibiotics are frequently used in conjunction with topical therapies such as azelaic acid, Benzoyl peroxide, and salicylic acid. Besides, aesthetic therapies such as facials are available for cystic acne therapy. In addition to antibiotic treatment, some physicians advocate oil and sebum management regimes.

Hydrogels are three dimensional (3D) cross-linked polymer networks that can absorb and hold significant amounts of water. Their unique characteristics, including high water content, softness, flexibility, and biocompatibility, make them extremely valuable materials. Hydrogels are made from natural and synthetic hydrophilic polymers that are physically or chemically cross-linked. Their adjustable features, as well as their tunable production processes and resemblance to living tissue, open up a plethora of biomedical applications.

Because of their gentle processing conditions and ability to integrate a wide range of bioactive compounds, hydrogel scaffolds are ideal for wound dressing. The hydrogel matrices encourage angiogenesis and re-epithelialization, as well as new extracellular matrix (ECM) synthesis and maturation. Hydrogel based drug delivery technologies have found potential clinical applications and can incorporate and subsequently release therapeutically active drugs with pinpoint precision in terms of time and space. Hydrogels can control the release of numerous therapeutic substances both spatially and temporally.

Owing to their advantages as an ECM like wound healing material and their potential to be utilized as a drug delivery system, hydrogel based formulations can find potential application in the topical treatment of cystic acne lesions. The cooling effect and softness is an additional benefit that can aid in the healing of inflamed acne skin. The precise subject of the present invention is a PVA/Linseed/ZnO based dually crosslinked nanocomposite hydrogel sheet and the acne patches loaded with doxycycline made from the fabricated sheet for topical treatment of cystic acne.

SUMMARY OF THE INVENTION

This invention relates to the synthesis of dually cross-linked Polyvinyl alcohol and linseed mucilage hydrogel sheets incorporating Zinc Oxide (ZnO) which is subsequently developed into doxycycline loaded acne patches.

Polyvinyl alcohol (10% w/v) solution is mixed with equal volume of 2% (w/v) linseed mucilage extract. Nano ZnO (5% w/v) is incorporated into the mix to utilize its antimicrobial potential. Citric acid (2% w/v) is added as a cross-linker. The resulting formulation is then subjected to 30 kGY electron beam on a conveyer belt at speed of 3 m/min. Dual covalent crosslinking is achieved via citric acid and exposure to electron beam and finally, flat non-toxic and biocompatible hydrogel sheets (3 mm thickness) are obtained. The hydrogel sheets are then mechanically cut into patches of 1 inch diameter. The patches upon drying were loaded with doxycycline to form medicated acne patches.

In an embodiment of the invention, the drug loaded patches are placed over adhesive tapes and covered on the other side with a polyethylene terephthalate (PET) sheet until application. In other embodiments of the invention, the patches are air dried before being attached to adhesive tapes and PET sheet. This embodiment would require skin to be wet before application.

The prepared hybrid PVA/Linseed nanocomposite hydrogel patches are found as excellent bacterial growth inhibitors in an in vitro analysis against *Staphylococcus aureus*, the bacterial strains primarily involved in the development of cystic acne.

DETAILED DESCRIPTION OF THE INVENTION

The invention described herein involves the synthesis of PVA/Linseed mucilage/ZnO nanocomposite hydrogel sheets and their subsequent development into doxycycline loaded acne patches. The embodiment disclosed provides several benefits over the conventional acne patches including biocompatibility, ECM like wound healing potential, cooling effect, anti-microbial potential and release of drug at the target site. The hydrogel sheet comprising PVA and Linseed is biocompatible and cheap, is impregnated with ZnO, dually crosslinked and subsequently loaded with doxycycline to develop into acne patches.

Synthesis of hydrogels: A 10% (w/v) Polyvinyl alcohol solution was made by dissolving the required amount of PVA in distilled water at 80° C. A homogenizer was employed to ensure thorough mixing of solution.

A 2% (w/v) linseed solution was prepared by suspending the required weight of dry linseeds in distilled water. The resulting mixture was allowed to stir at 60° C. for two hours following which the mucilage extract was strained using a strainer.

Equal volumes of 10% polyvinyl alcohol and 2% Linseed mucilage extract were mixed together and 2% (w/v) citric acid was added to it. The resulting mixture was allowed to stir for 30 minutes to yield PVA/LS based formulations For the preparation of ZnO based formulation, 0.5% (w/v) of ZnO was added to the above mixture and the mixture was homogenized thoroughly to yield PVA/LS/ZnO based formulation.

Figure 1:
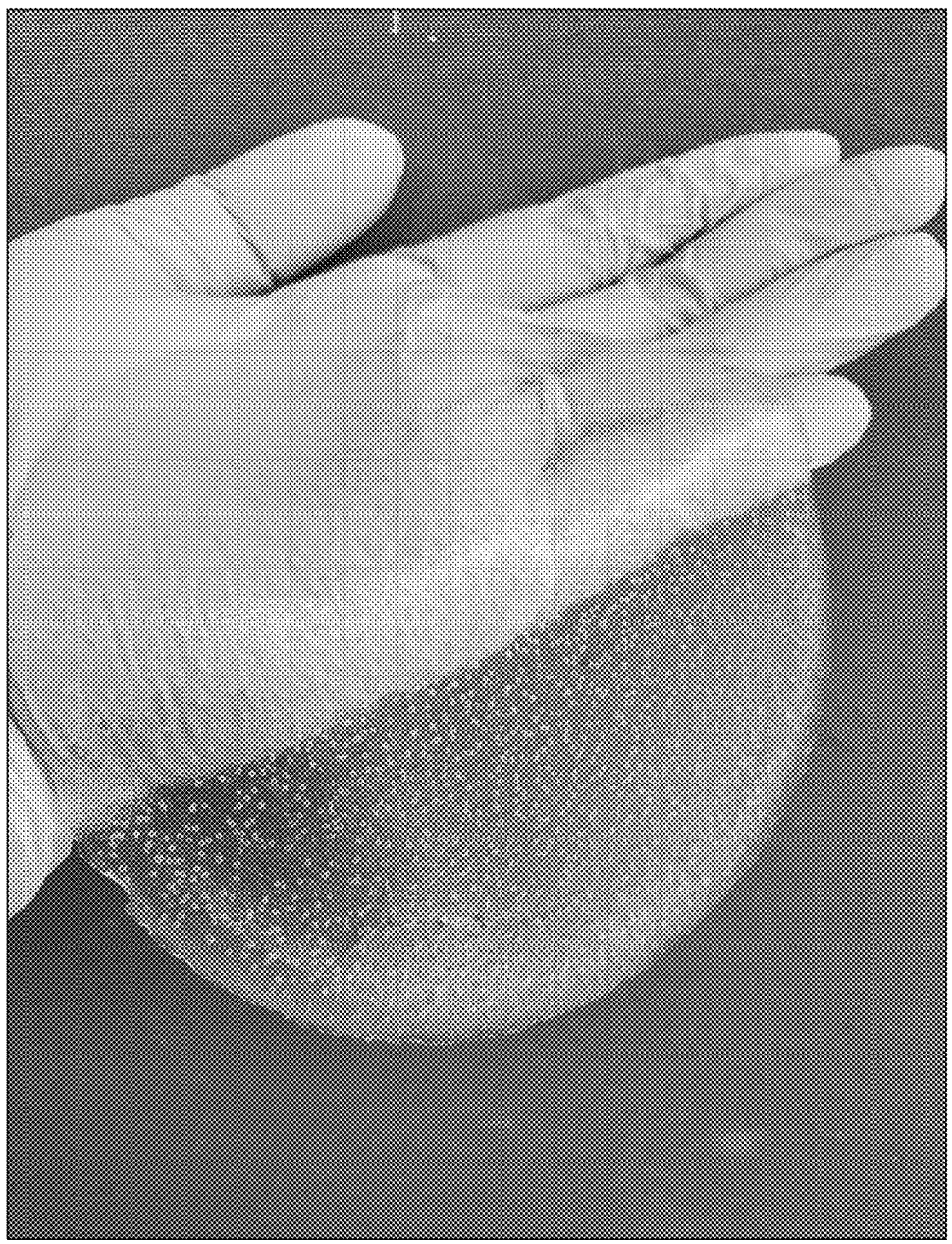
FIG. 1 represents a photograph of the synthesized hydrogel sheet.

The above formulations (were poured into polystyrene trays and exposed to 30 KGY electron beam intensity at a conveyer belt speed of 3 m/min following which they assumed a sheet like morphology; individual sheets being 3 mm in thickness as shown in FIG. 1.

Figure 2:
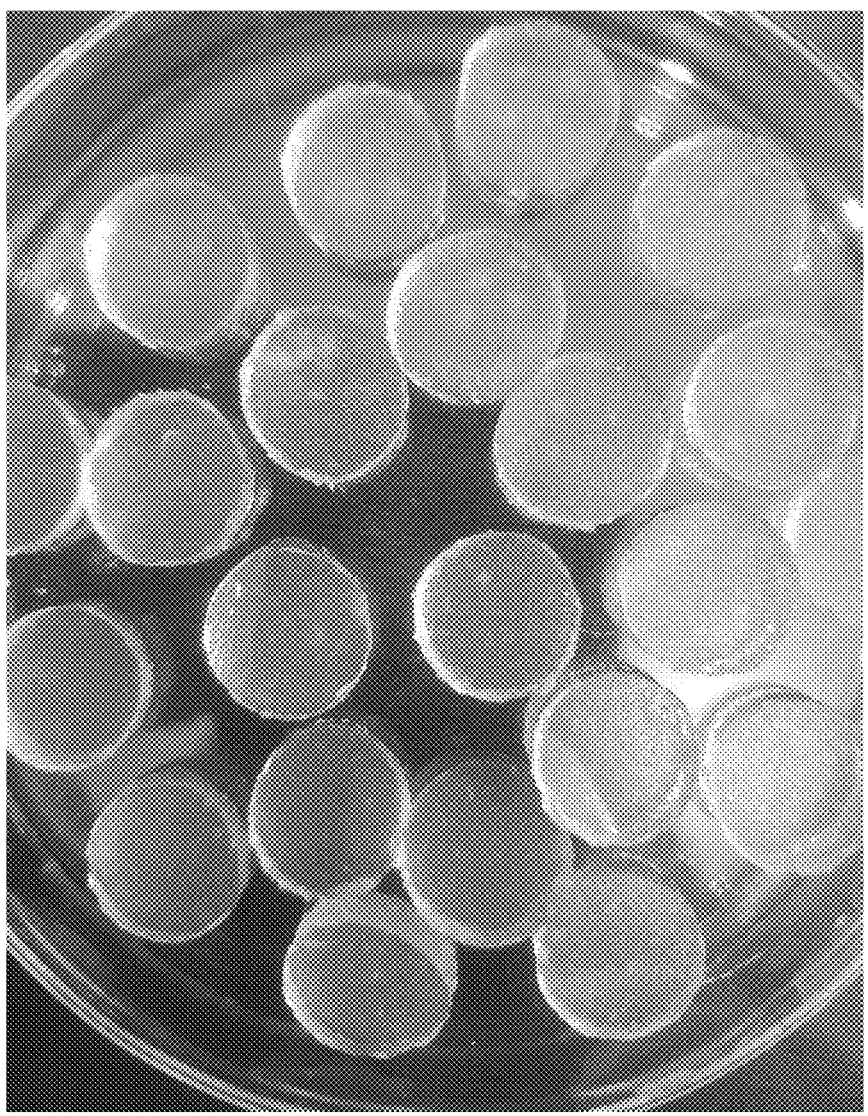
FIG. 2 represents a photograph of PVA/LS/ZnO hydrogel Patches of 1 inch diameter.
Figure 3:
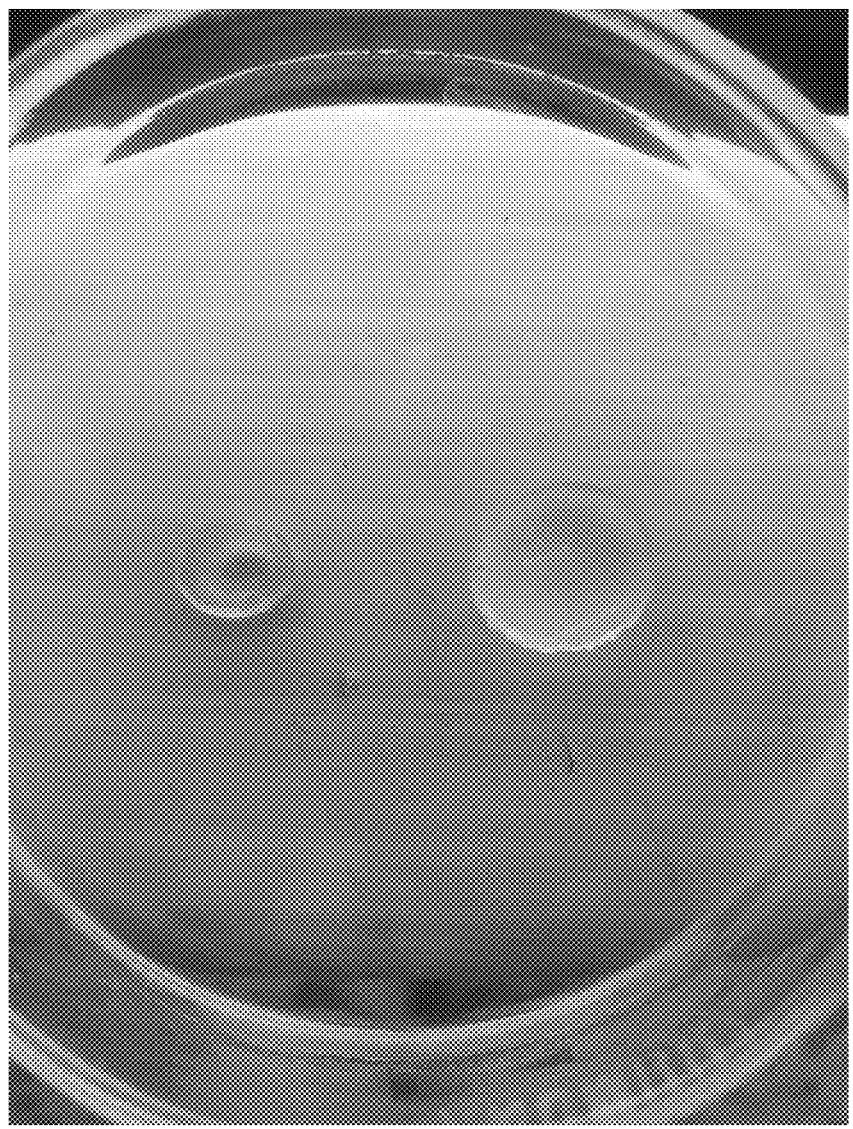
FIG. 3 shows a photograph representing dried vs swollen PVA/LS/ZnO hydrogel disk.

Fabrication of acne patches: The freshly prepared sheet hydrogels were cut into circular patches of 1 inch diameter (as shown in FIG. 2) and allowed to dry in a vacuum oven at 50° C. before they were immersed in 3 uM doxycycline solution for drug loading. The dry and freshly prepared hydrogels sheet are shown in FIG. 3.

Figure 4:
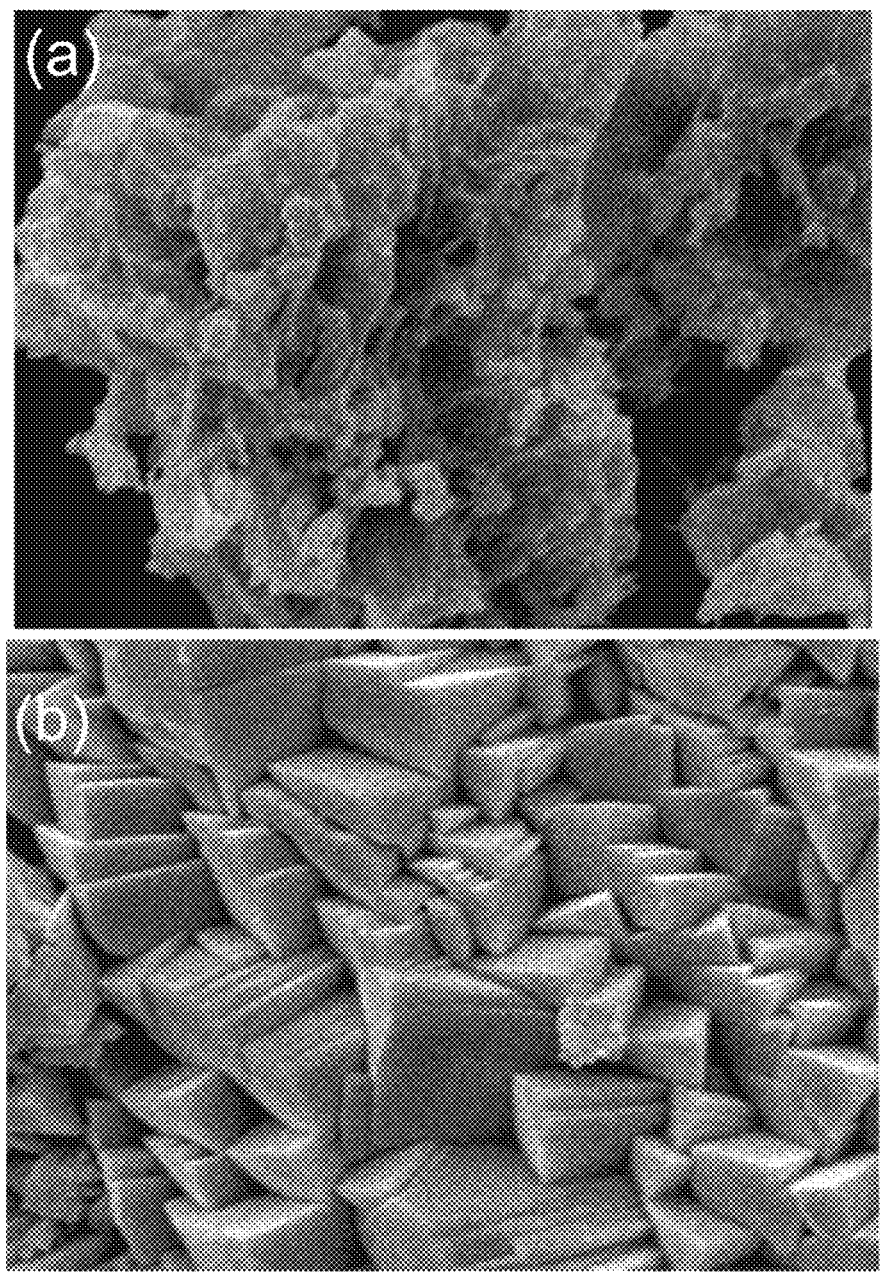
FIG. 4 is the SEM micrographs of (a) PVA/LS hydrogel (b) PVA/LS/ZnO hydrogel.

The PVA/LS and PVA/LS/ZnO hydrogel sheets after freeze drying were analyzed for their surface morphology by scanning electron microscopy (HVSEM) (Model; JSM-5300, Japan). FIG. 4 (a and b) shows the surface of morphology of the hydrogel sheets. The PVA/LS hydrogel sheet manifests a porous honey comb like microstructure with random closed to open cells and pore size lying in the range of 100-400 nm (0.1-0.4 μm).

SEM analysis of the PVA/LS/ZnO as shown in FIG. 4(b) revealed a transition to nanocrystalline morphology with aggregates of ZnO nanostructures adorning the hydrogel sheet surface.

Figure 5:
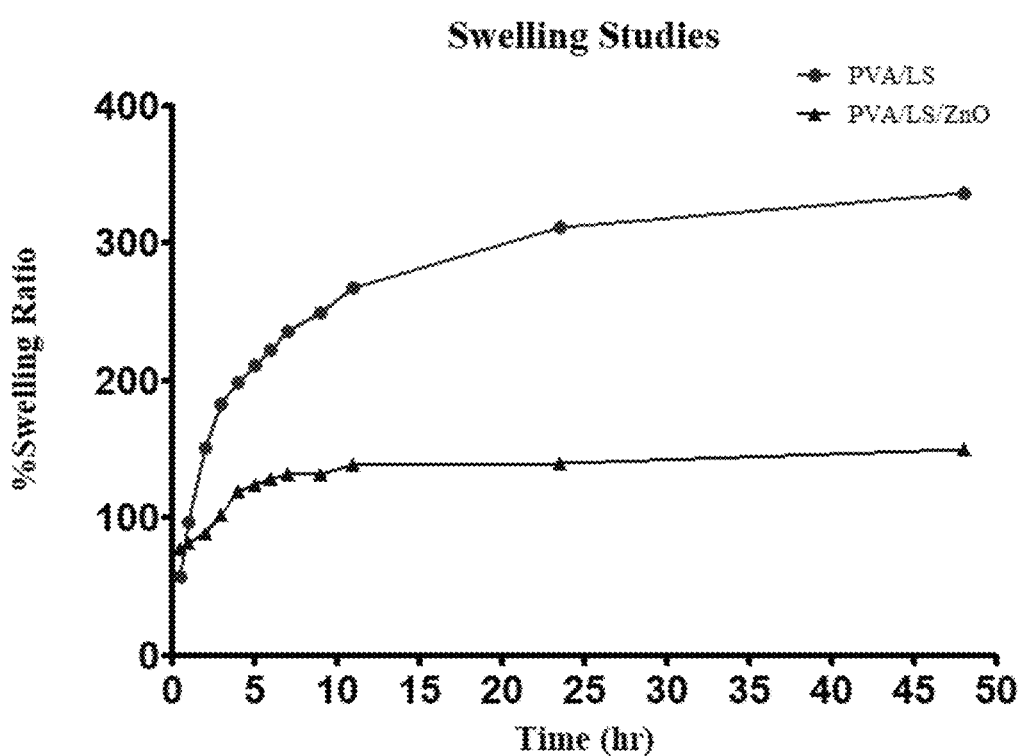
FIG. 5 shows the swelling behavior of PVA/LS and PVA/LS/ZnO hydrogel.

Swelling behavior is an intrinsic property of hydrogels, where the hydrogels expand due to solvent penetration into the voids between the polymeric chain networks. For swelling experiments, fresh hydrogel sheets were cut into 3 cm×3 cm squares and were kept in oven to dry until constant weight. The dried squares were immersed in distilled water and their weight was periodically measured after wiping the excess water using tissue paper (FIG. 3). The timed water absorption percentages of hydrogels are presented in FIG. 5. Both PVA/LS and PVA/LS/ZnO hydrogels manifested a fast swelling behavior, swelling rather quickly in the first 10 hours, following which they attained an equilibrium swelling after a passage of 45 hours. The integrity of the sheet/disk remained unaffected in the swelling process and even after a week of immersion in distilled water. The percent swelling of PVA/LS/ZnO was evidently less than PVA/LS hydrogels since the incorporated ZnO particles occupied quite many of the water binding sites within the hydrogel network.

Figure 6:
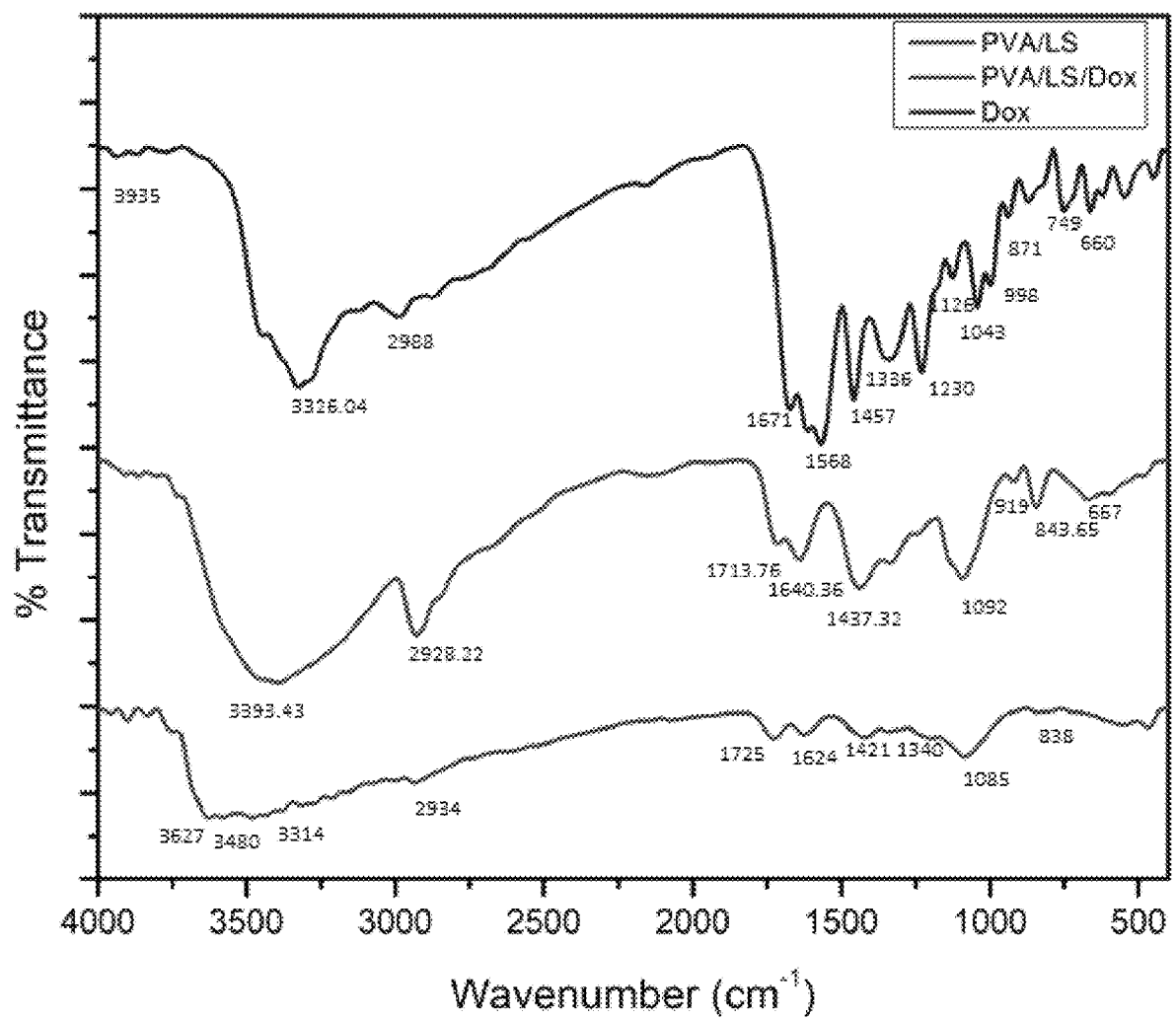
FIG. 6 is a comparison of the IR spectra of PVA/LS, PVA/LS/Dox and Doxycycline.
Figure 7:
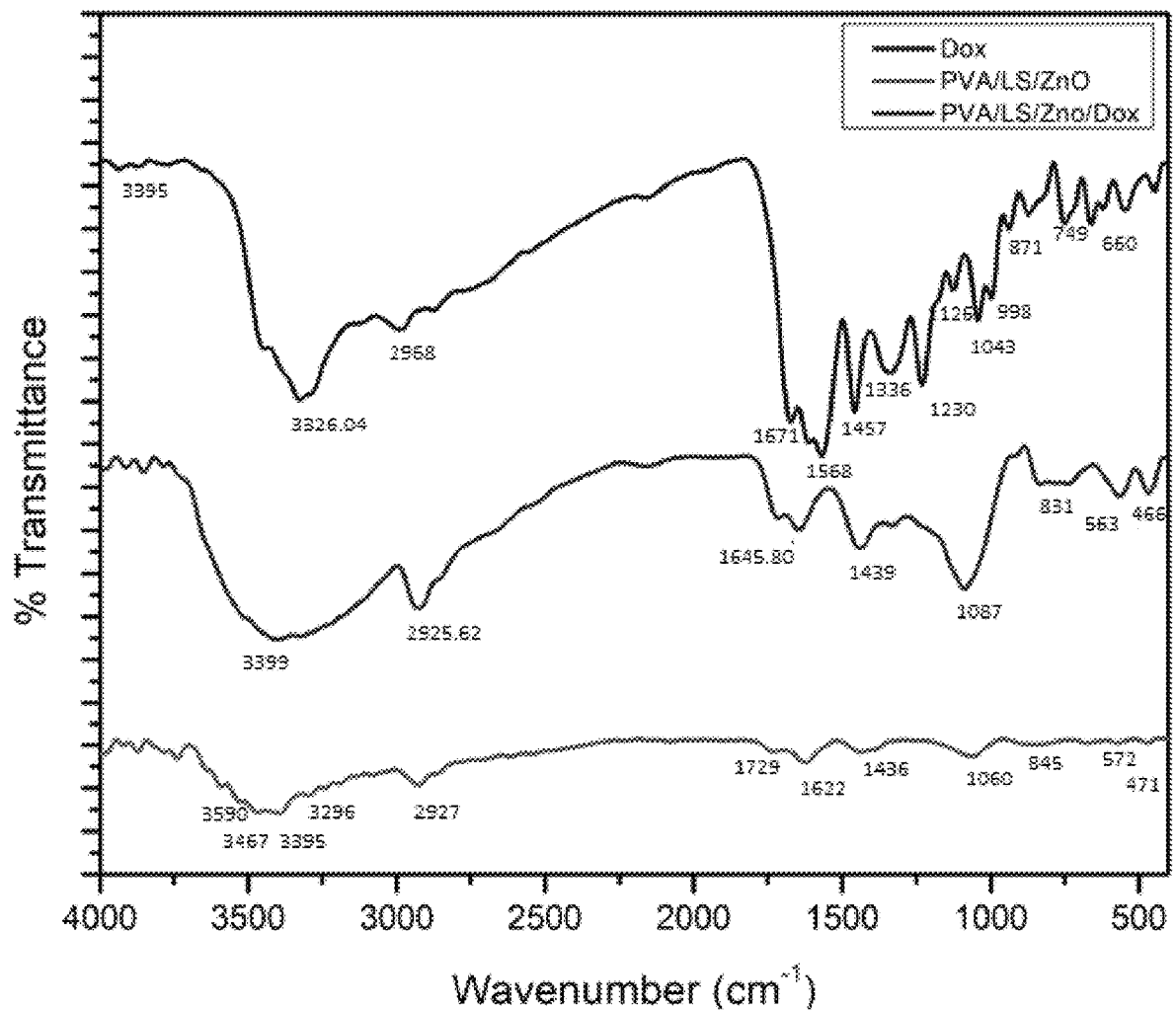
FIG. 7 is a comparison of the IR spectra of PVA/LS/ZnO, PVA/LS/ZnO/Dox and Doxycycline.

For drug loading and in vitro bacterial growth inhibition assay individual dried disks of PVA/LS and PVA/LS/ZnO hydrogel were subsequently immersed in a 0.3 μM doxycycline solution for 48 hours. The individual disks loaded approximately 45±0.5 μg of doxycycline. IR spectroscopy was carried out to verify the successful loading of doxycycline within the disks. As shown in FIG. 6 and FIG. 7, the appearance of specific peaks in the IR spectrum confirmed the successful loading of the drug in the PVA/LS and PVA/LS/ZnO hydrogel disk. In both spectra the peak appearing in the region of 3400 $cm^{-1}$ to 3550 $cm^{-1}$ corresponds to —OH of the hydrogel network. The peaks at 2932 $cm^{-1}$, 2940 $cm^{-1}$, and 1450 $cm^{-1}$ are due to the —CH vibration and stretching. The aryl —C=O stretch at 1635 $cm^{-1}$, aromatic —C=C ring stretch bands at 1520 $cm^{-1}$ and peaks at 1238 $cm^{-1}$, 1047 $cm^{-1}$ arising from stretching of C—O in phenols and —C—O—C stretch and bending in ketones are all characteristic peaks arising from the tetracycline structure of doxycycline. In FIG. 7, the peak at 544 $cm^{-1}$ corresponds to ZnO.

Figure 8:
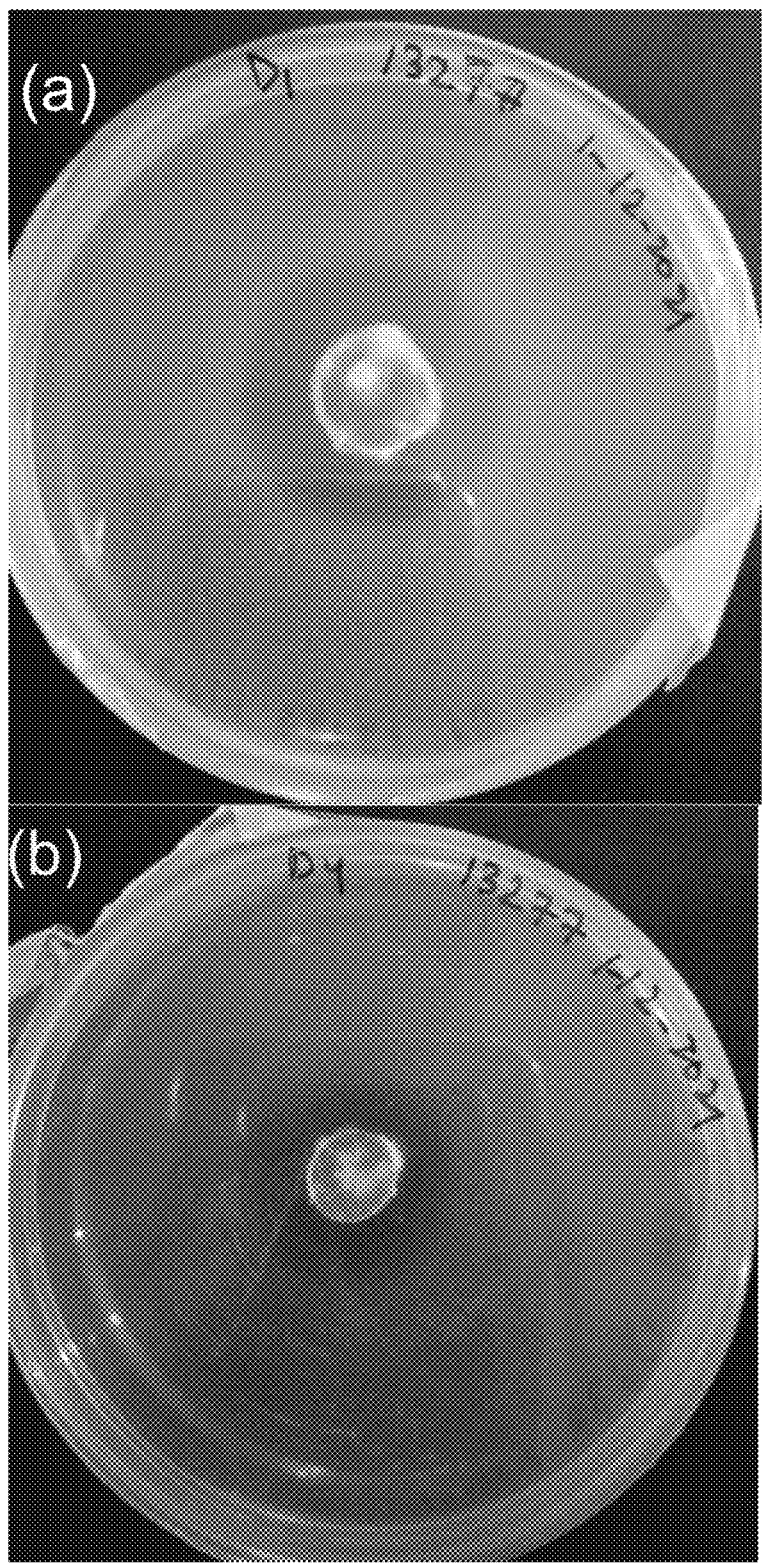
FIG. 8 shows the In vitro bacterial growth inhibition observed after 24 hrs for (a) PVA/LS/Dox (b) PVA/LS/ZnO/Dox

In the in vitro bacterial growth inhibition assay against *S. aureus* the PVA/LS/Dox and PVA/LS/ZnO/Dox hydrogel disks respectively manifested a zone of inhibition (ZOI) equal to 2.5±0.1 cm and 3.1±0.1 cm after 24 hours with respect to the control as shown in FIG. 8.

The invention claimed is:

1. A nanocomposite hydrogel sheet acquired from dual crosslinking of a polymeric mixture comprising 10% w/v Polyvinyl alcohol and 2% Linseed mucilage extract and ZnO nanoparticles by citric acid and 30 KGY electron beam exposure.

2. The nanocomposite hydrogel sheet according to claim 1, wherein the polymeric mixture was an equivolume mixture of 10% w/v PVA and 2% Linseed mucilage extract.

3. The nanocomposite hydrogel sheet according to claim 1, wherein the quantity of ZnO added was 0.5% w/v of the total polymeric mixture.

4. The nanocomposite hydrogel sheet according to claim 3, wherein 1 inch acne patches cut from the hydrogel sheet loaded with a 3 uM solution of the tetracycline antibiotic doxycycline, manifested a bactericidal potential against *Staphylococcus aureus* in an in vitro bacterial growth inhibition assay.

5. The nanocomposite hydrogel patches according to claim 4, wherein it is the first doxycycline containing wet hydrogel based formulation prepared for topical treatment of cystic acne lesions.

* * * * *